United States Patent [19]

Fisher

[11] Patent Number: 4,534,971
[45] Date of Patent: Aug. 13, 1985

[54] COMPLEXATION OF ANTHRACYCLINE AND ANTHRAQUINONE ANTIBIOTICS BY THE APO RIBOFLAVIN BINDING PROTEIN FROM EGGS

[75] Inventor: Jed F. Fisher, Minneapolis, Minn.

[73] Assignee: Regents of the University of Minnesota, Minneapolis, Minn.

[21] Appl. No.: 435,616

[22] Filed: Oct. 20, 1982

[51] Int. Cl.$^3$ .................... C12N 11/02; A01N 31/00; C07C 103/52; C07G 7/00; A23J 1/00; C12P 19/56

[52] U.S. Cl. ................................ 514/21; 260/112 R; 260/112 B; 260/112.5 R; 424/18; 435/78; 514/251

[58] Field of Search .......................... 424/177, 180, 18; 260/112.5 R, 112 B, 112 R; 536/6.4; 435/78

[56] References Cited

PUBLICATIONS

Bitman, J. et al, *Chemical Abstracts*, vol. 93, 1980, No. 234179, "Cholesterol . . . Various Avian Species".
Peterson, D. W., *Chemical Abstracts*, vol. 88, 1978, No. 188323b, "Composition and Cholesterol . . . ".
Walsh, C., et al, (1978), *Biochemistry*, vol. 17, pp. 1942-1951.
Kituchi, K. et al, *Biochimica et Biophysica Acta*, vol. 434, (1976), pp. 509-512.
Fisher, Jed et al., 1982, *Biochemistry*, vol. 21, No. 24, 6172-6180.
Choi, J. and McCormick, D., (1980), *Ar. Biochem. Biophys.*, 204, 41-51.
Walsh, C., et al, (1978), *Biochemistry*, 17, 1942-1951.
Blankenhorn, G., (1978), *Eur. J. Biochem.*, 82, 155-160.
Kitagawa, T., et al, (1979), *Biochemistry*, 18, 1804-1808.
Arcamone, F., (1981), *Med. Chem-Monographs*, 17, 39-40, and 112-114.
Abuchowski, A., et al, (1977), *J. Biol. Chem.*, 252, 3578-3581; 3582-3586.
Lee, T., Sokoloski, T. and Royer, G., (1981), *Science*, 213, 233-235.
Becvar, J. and Palmer, G., (1982), *J. Biol. Chem.*, 257, 5607-5614.

*Primary Examiner*—Thomas G. Wiseman
*Assistant Examiner*—Robin L. Teskin
*Attorney, Agent, or Firm*—Burd, Bartz & Gutenkauf

[57] ABSTRACT

A method for the preparation of light-stable water-soluble complexes of antitumor antibiotics and binding protein and the resulting products. The antibiotics are of the anthracycline and anthraquinone classes, as defined. The binding protein is purified apo riboflavin binding protein from eggs. The complexes are prepared by admixing solutions of the antibiotic and protein in substantially equimolar proportions. The complexes are useful for preparing stable aqueous solutions of the antibiotics for oral delivery and for redox titrations of anthracyclines.

15 Claims, No Drawings

COMPLEXATION OF ANTHRACYCLINE AND ANTHRAQUINONE ANTIBIOTICS BY THE APO RIBOFLAVIN BINDING PROTEIN FROM EGGS

BACKGROUND OF THE INVENTION

1. Field of the Invention

This invention is directed to a method for the preparation of stable complexes of antitumor antibiotics of the anthracycline and anthraquinone classes with purified apo riboflavin binding protein from eggs, and the resulting products.

The anthracyclines and anthraquinones are a known family of antitumor antibiotics used widely for the palliative treatment of cancer. These antibiotics exhibit a number of undesirable chemical and biological properties. Some of the adverse chemical properties are poor water solubility and light-induced degradation. Some of the adverse biological properties are acute and chronic toxicity to the patient. In an effort to minimize these undesired properties, a large number of derivatives have been prepared, new methods for drug delivery explored, and various drug conjugates and complexes prepared. The present invention provides a new basis for the development of an optimal formulation for specific delivery, or controlled release of the antibiotic.

2. The Prior Art

The white and yolk of eggs contain abundant quantities of a riboflavin binding protein. This protein binds, with varying affinity, a large number of riboflavin derivatives and analogs. For these reasons it has been used frequently for the characterization of the flavin binding site using different spectroscopic probes. There is no known report, however, of this protein binding molecules structurally unrelated to the flavin (isoalloxazine) ring system.

Several methods for the conjugation or complexation of anthraquinone antibiotics have been described: covalent attachment to immunoglobulins and dextrans, intercalated into DNA fragments, and as a ferric ion complex. None have any significant advantage over the free drug for therapeutic administration, nor do any correspond to a specific complexation by a protein macromolecule. Although non-specific protein complexation of anthracycline antibiotics has been observed, they have been relatively unstable.

SUMMARY OF THE INVENTION

Broadly stated the present invention is directed to a method for the preparation of stable water-soluble complexes of antitumor antibiotics of the anthracycline and anthraquinone classes with purified apo riboflavin binding protein from eggs which comprises preparing water miscible solutions of the antibiotic and protein and admixing the solutions. The antibiotic and protein are admixed in approximately equimolar proportions. One mole of antibiotic is bound per mole of protein. The complex may be concentrated by ultrafiltration or ion exchange chromatography, and stored for short periods in cold, sterile solution or longer periods as the lyophilized powder. The complexes are stable and may be used in the therapeutic administration of the antibiotic. The complexes also permit titrations of redox-active antibiotics, i.e., those which require the addition and transfer of electrons for their therapeutic activity, in vivo, which are not possible with the free anthracycline.

The invention includes the light-stable water-soluble antibiotic-protein complexes as new compositions of matter.

DETAILED DESCRIPTION OF THE PREFERRED EMBODIMENTS

The egg apo riboflavin binding protein is obtained in homogeneous form from chicken egg white by acid treatment, DEAE (diethylaminoethyl) Sephadex chromatography, and sulfopropyl-Sephadex chromatography, according to the procedure of Becvar, J. (1973) Ph.D. thesis, University of Michigan. The purified protein may be stored, for example, frozen at $-20°$ C. in 10 mM potassium phosphate, 1 mM EDTA pH 7.0 buffer, at concentrations between about 1 and 10 mM. The isolated yield is approximately 15 mgs. (0.37 $\mu$mol) per egg. The protein is stable as a sterile solution and as a lyophilized powder in both its apo and drug-complexed forms.

The binding site of the egg binding protein has been described. Binding of riboflavin occurs primarily by the energetically favorable displacement of water from a hydrophobic cavity, supplemented by particularly favorable hydrophobic contacts, hydrogen bonds, and steric compatability. The binding site prefers neutral molecules or zwitterions, tolerates cations and eschews anions. Deviation from ring planarity is disliked. Like the flavins, anthracyclines and anthraquinones are linear, planar conjugated molecules. While they do not duplicate features that are advantageous to the flavin, neither do they possess substituents that would intrude on sterically forbidden regions.

The antibiotics which can be complexed include the anthracyclines having the formula:

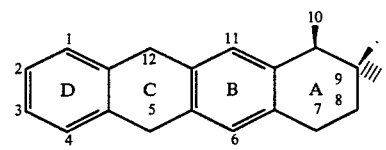

in which ring positions 4, 5, 6, 7, 9, 10, 11 or 12 may be substituted. Positions 5 and 12 have $=$O or OH, which are the same. When positions 5 and 12 are $=$O, positions 4, 6 and 11 may have H, OH or OCH$_3$, which may be the same or different. When positions 5 and 12 have OH, positions 6 and 11 have $=$O. Virtually any substituent may be at the 7, 9 or 10 positions without adversely affecting the binding capabilities of the anthracyclines. By way of example, position 7 may have 7S or 7R chirality due to OCH$_3$ or any mono-, di-, or trisaccharide substituent, position 9 may have 9S or 9R chirality due to OH and either CH$_3$, C$_2$H$_5$, COCH$_2$OH or COCH$_2$OR where R is an ether or ester functional group; and position 10 may have 10S or 10R chirality due to COCH$_3$, CO$_2$CH$_2$CH$_3$ or CO$_2$H. Exemplary anthracyclines are shown in Table I.

Although less tightly bound, anthraquinone antibiotics which can be complexed include those having the formula:

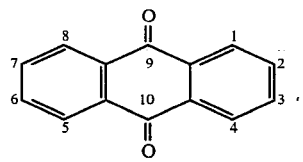

in which positions 1, 4, 5 and 8 may be substituted. Positions 1 and 4 may have H or OH. Positions 5 and 8 may have $N(CH_2)_2NH_2^+(CH_2)_2OH$ or any bis[(hydroxy alkyl)amino]alkyl side chain. Exemplary anthraquinones include 1,4-dihydroxy-5,8-bis[[2-(hydroxyethyl)amino]ethyl]-9. 10-anthracenedione (DHAQ).

Derivatives and metabolites of the anthracycline and anthraquinone antibiotics may be complexed with the binding protein. Exemplary materials include daunomycin hydrochloride, AD-32 (a diacylated derivative of adriamycin), anthracyclinols, anthracyclinones(aklavinone, 7-deoxydaunomycinone and iso-7-deoxydaunomycinone), 7-deoxyanthracyclinones, and the like.

The protein-antibiotic complex is prepared by admixture of solutions of the antibiotic and of the protein in substantially equimolar proportions. One mole of antibiotic is bound per mole of protein. The protein is dissolved in water. The antibiotic is dissolved in water or water miscible organic solvent, depending upon its solubility.

tions of the complex at concentrations of 1 mM are prepared easily. The light instability of the antibiotic is minimized as a consequence of efficient energy transfer to an aromatic amino acid present in the binding site. Thus, complexation is accompanied by the complete quenching of the antibiotic fluorescence. Because no compound is more tightly bound by the egg binding protein than riboflavin, the antibiotic can be released from the complex by admixing a solution of the complex with a solution of riboflavin.

The complex may be prepared as a freely water-soluble, light-stable sterile solution suitable for oral delivery of the antibiotic. The complex is suitable for further modification into a non-immunogenic form capable of controlled drug release following i.p. or i.v. administration.

Although chicken eggs are the preferred source of riboflavin binding protein because of their ready availability in large quantities, eggs of other fowl such as ducks, geese, turkeys and the like are also sources of binding protein and may be used.

A further use of the antibiotic-protein complex is in redox titrations. Aqueous redox titrations of anthracyclines cannot be done. Although anthracycline glycosides are water soluble, loss of the glycoside (with its positive charge) provides the almost completely water insoluble 7-deoxyanthracyclinones. Unfortunately, glycoside loss is an integral aspect of anthracycline redox chemistry. The binding protein-anthracycline complex has been used for anaerobic aqueous redox titrations.

TABLE 1

| Compounds | 4 | 5 | 6 | 7 | | 9 | 10 | 11 | 12 |
|---|---|---|---|---|---|---|---|---|---|
| Adriamycin | $OCH_3$ | =O | OH | S—L-daunosamine | R | —$COCH_2$OH / —OH | H | OH | =O |
| AD-32 | $OCH_3$ | =O | OH | S—N—trifluoroacetyl-daunosamine | R | —$COCH_2OCO(CH_2)_4CH_3$ / OH | H | OH | =O |
| Aclacinomycin-A | OH | =O | OH | S—L-rhodosamine-2-deoxy-L-fucose-L-cinerulose | R | —$CH_2CH_3$ / —OH | R—$CO_2CH_3$ | H | =O |
| Daunomycin | $OCH_3$ | =O | OH | S—L-daunosamine | R | —$COCH_3$ / —OH | H | OH | =O |
| 4-Demethoxy daunomycin | H | =O | OH | S—L-daunosamine | R | —$COCH_3$ / —OH | H | OH | =O |
| 7-9-Diepi-4-demethoxy-daunomycin | H | =O | OH | R—L-daunosamine | S | —$COCH_3$ / —OH | H | OH | =O |
| Aklavinone | OH | =O | OH | S—OH | R | —$CH_2CH_3$ / —OH | R—$CO_2CH_3$ | H | =O |
| 7-Deoxydaunomycinone | $OCH_3$ | =O | OH | H | R | —$COCH_3$ / —OH | H | OH | =O |
| Iso-7-deoxy-daunomycinone | $OCH_3$ | OH | =O | H | R | —$COCH_3$ / —OH | H | =O | OH |

The solutions are agitated sufficiently to homogenize the mixture. The concentration of the solutions may be between about 1 to 10 mM. The complexation may be carried out at temperatures between about 0° to 45° C., but preferably at ambient temperatures of about 20° to 30° C. The complex may be formed at pH between about 3.8 and 10, but preferably between about 5 and 8.

The complex may be concentrated by ultrafiltration or ion exchange chromatography, and stored for short periods in cold, sterile solution or longer periods as the lyophilized powder. In this formulation, the antibiotic solubility is limited only by the protein solubility; solu- Dithionite reduction of the anthracycline glycoside provides, in a 2e$^-$ process, the 7-deoxyanthracyclinone, via reductive elimination. The bound 7-deoxyanthracyclinone is then further 2e$^-$ reduced to the bound hydroquinone. Semi-quinone radical intermediates are observed transiently; these are stable neither in solution nor complexed to the binding protein. Oxidation of the hydroquinone is accomplished by several reagents (oxygen, hydrogen peroxide, ferricyanide, cytochrome c). In the case of 7-deoxydaunomycinone hydroquinone, a mixture of two products is produced upon oxidation; these are the chromo 7-deoxydaunomycinone (identical to the first 2e⁻ reduction intermediate) and its leuco isomer, 8-acetyl-7,8,9,10-tetrahydro-5,8,12-trihydroxy-1-methoxy-6,11-napthacenedione(iso-7-deoxydaunomycinone).

The invention is further illustrated by the following examples.

EXAMPLE 1

A working solution of adriamycin was obtained by dissolution in warm 0.035M potassium phosphate pH 7.0 buffer containing 0.15M NaCl and 0.5 mM EDTA and cooled to ambient temperature (24±2° C.). To a 3.0 mL solution containing 3 $\mu$M adriamycin was added 5.0 $\mu$L increments of a 0.49 mM binding protein solution in 10 mM potassium phosphate, 1 mM EDTA pH 7.0 buffer. The binding protein solution was added until at least 85% of the adriamycin was bound, approximately 45 $\mu$L binding protein solution total. The equilibrium constant for dissociation ($K_d$) was determined to be 0.5±0.1 $\mu$M indicating good binding of the adriamycin with the binding protein.

EXAMPLES 2–7

The more general ability of the binding protein to complex anthracycline glycosides was determined with the anthracycline glycosides nogalomycin, aclacinomycin A, daunomycin, 4-demethoxydaunomycin, 7,9-diepi-4-demethoxydaunomycin, and N-trifluoroacetyl-14-valeryl-adriamycin (AD-32). Nogalomycin was dissolved in concentrated solution in dimethylformamide and the solution concentration determined by dilution into alcohol. Aclacinomycin A was dissolved in dimethylformamide and then diluted into buffer to give a final dimethylformamide concentration of 1% or less. Daunomycin was dissolved in warm buffer, followed by cooling. 4-Demethoxydaunomycin and its epimer were dissolved directly in water. AD-32 was dissolved in dimethylformamide. The general procedure of Example 1 was followed, except as to AD-32. The binding protein solution was added incrementally until most or all of the anthracycline glycoside was bound. The nonaqueous solution of AD-32 was added to an aqueous solution of the binding protein. The dissociation constants are shown in the table:

| Example: | | $K_d$ ($\mu$M) |
|---|---|---|
| (2) | Nogalomycin | >1000 |
| (3) | AD-32 | — |
| (4) | Aclacinomycin A | 1.0 |
| (5) | Daunomycin | 0.4 |
| (6) | 4-Demethoxydaunomycin | 0.3 |
| (7) | 7,9-Diepi-4-demethoxydaunomycin | 0.08 |

All save nogalomycin bind. Aclacinomycin A, daunomycin and 4-demethoxydaunomycin bind with an affinity hardly different than that of adriamycin. 7,9-Diepi-4-demethoxydaunomycin binds most tightly of all. AD-32 binds well, but aqueous insolubility precludes quantitative determination. The most important observations are the tight binding of AD-32 and aclacinomycin A. AD-32 is a diacylated derivative of adriamycin with distinctly different pharmacological properties. It is also utterly insoluble in water. Nonetheless the addition of AD-32 as a concentrated solution in dimethylformamide to an aqueous solution of a slight molar excess of the apo binding protein, to give final concentrations of each of approximately 20 $\mu$M, results in the quantitative formation of the AD-32-binding protein complex. In contrast, dispersal of the AD-32 dimethylformamide solution in the same buffer without the binding protein results in the instantaneous precipitation of the AD-32. Due to this insolubility titration studies are not feasible.

EXAMPLES 8–10

The binding protein affinity of three anthracyclinones was determined: (±)-aklavinone, 7-deoxydaunomycinone and iso-7-deoxydaunomycinone. Aklavinone and 7-deoxydaunomycinone were made as concentrated solutions in dimethylformamide, and the solution concentrations determined by dilution into alcohol. Leuco iso-7-deoxydaunomycinone was dissolved in dimethylformamide and diluted into buffer. The general procedure of Example 1 was followed. The dissociation constants are shown in the table:

| Example: | | $K_d$ ($\mu$M) |
|---|---|---|
| (8) | 7-Deoxydaunomycinone | 0.08 |
| (9) | (±)-Aklavinone | 0.02 |
| (10) | Iso-7-deoxydaunomycinone | 0.02 |

The anthracyclinones were found to be bound significantly more strongly than the parent anthracycline glycosides. Within the limits of detection, both enantiomers of the racemic aklavinone (7S, 9R, 10R, and 7R, 9S, 10S) are equally well bound. Also of interest is the high affinity of the binding protein for iso-7-deoxydaunomycinone(8-acetyl-7,8,9,10-tetrahydro-5,8,12-trihydroxy-1-methoxy-6,11-napthacenedione). This compound is a kinetic product of 7-deoxydaunomycinone hydroquinone oxidation. Although not stable in aqueous buffer to isomerization to 7-deoxydaunomycinone, this material is stable in organic solvents and when complexed to the binding protein.

EXAMPLES 11–15

Further experiments were undertaken to determine the binding protein's capabilities as to several anthraquinones and anthraquinone-like molecules:

| Example: | |
|---|---|
| (11) | Tetracycline |
| (12) | Carminic acid |
| (13) | 1,4Dihydroxy-5,8-bis-[[2-(hydroxyethyl)amino]ethyl]-9,10-anthracenedione (DHAQ) |
| (14) | Chlorpromazine |
| (15) | Quinacrine |

Solutions were prepared and admixed as previously described. Within the limits of spectrophotometric detection ($K_d$>250 $\mu$M) neither tetracycline nor carminic acid (an insect feeding deterrent) bind. The interesting antitumor antibiotic DHAQ is bound weakly ($K_d$=60 $\mu$M). The high affinity of the binding protein for chlorpromazine ($K_d$-1 $\mu$M) and quinacrine ($K_d$-0.2 $\mu$M) is significant as both these are known to complex to flavin-dependent enzymes.

EXAMPLE 16

An anaerobic redox titration of the daunomycin-binding protein complex was done. The reducing agent used was dithionite anion. Spectrophotometric titrations were made on a Cary 219 spectrophotometer. Anaerobic titrations were done with gas tight syringes, with the deoxygenated solutions maintained under a positive pressure of $O_2$-free nitrogen. Dithionite was freshly prepared in $O_2$-free buffer and standardized by anaerobic riboflavin titration. Equilibration with dithionite is in all instances complete in seconds. Daunomycin is first converted in a $2e^-$ process to 7-deoxydaunomycinone, with reductive elimination of the glycoside. Assignment of structure to this titration intermediate was confirmed by its isolation, and chromatographic comparison with an authentic sample. Further dithionite addition reduces the bound 7-deoxydaunomycinone to a new chromophore ($\lambda_{max}=407$ nm). The hydroquinone is not further reduced, but is very easily oxidized upon mixing with oxidants such as oxygen, hydrogen peroxide, ferricyanide and cytochrome c. The absorption spectrum obtained following complete oxygen oxidation of the hydroquinone is different than any previous spectrum. Longer wavelength features, indicating the presence of 7-deoxydaunomycinone, are seen but a new chromophore ($\lambda_{max}$ approximately 445 nm) is also present. The structure of the compound corresponding to this chromophore is iso-7-deoxydaunomycinone on the basis of its spectroscopic data. In neutral aqueous buffer in the absence of the binding protein this compound promptly isomerizes to 7-deoxydaunomycinone ($k=6\times10^{-4}s^{-1}$). As the binding protein-complexed species it is, however, stable for days. Binding protein stabilization is also reflected in an estimated 10-fold slower rate of dithionite reduction of the iso-7-deoxydaunomycinone compared to either 7-deoxydaunomycinone or daunomycin. Of these three oxidized quinones it is the one preferentially bound by the riboflavin binding protein.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A method for the preparation of stable complexes of antitumor antibiotics of the anthracycline and anthraquinone classes with purified apo riboflavin binding protein from eggs which comprises:
   (A) preparing a water miscible solution of an antibiotic of the class consisting of (1) anthracyclines having the formula:

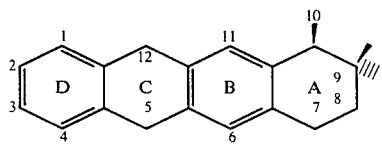

wherein positions 4, 5, 6, 7, 9, 10, 11 or 12 may be substituted, positions 5 and 12 have =O or OH, positions 4, 6 and 11 may have H, OH or OCH$_3$ when positions 5 and 12 have =O, positions 6 and 11 have =O when positions 5 and 12 have OH, position 7 may have 7S or 7R chirality due to OCH$_3$ or any mono-, di- or trisaccharide substituent, position 9 may have 9S or 9R chirality due to OH and either CH$_3$, CH$_2$CH$_3$, COCH$_2$OH or COCH$_2$OR where R is an ether or ester functional group, and position 10 may have 10S or 10R chirality due to CO$_2$CH$_3$, CO$_2$CH$_2$CH$_3$ or CO$_2$H, and (2) anthraquinones having the formula:

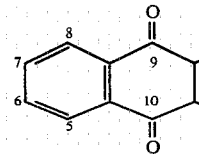

wherein positions 1, 4, 5 and 8 may be substituted, positions 1 and 4 having H or OH and positions 5 and 8 may have N(CH$_2$)$_2$NH$_2$+(CH$_2$)$_2$OH, or any bis[(hydroxyalkyl)amino]alkyl side chain,
   (B) preparing an aqueous solution of purified apo riboflavin binding protein from eggs, and
   (C) admixing the solutions in substantially equimolar proportions of antibiotic to protein to form a complex.

2. A method according to claim 1 wherein said riboflavin binding protein is from chicken eggs.

3. A method according to claim 1 wherein the concentrations of the solutions of antibiotic and protein are each between about 1 and 10 mM.

4. A method according to claim 1 wherein the solutions of antibiotic and protein are admixed by agitation sufficient to homogenize the solutions at a temperature between about 0° and 40° C.

5. A method according to claim 1 wherein the solutions of antibiotic and protein are admixed at a pH between about 3.8 and 10.

6. A method according to claim 5 wherein the solutions of antibiotic and protein are admixed at a pH between about 5 and 8.

7. A method according to claim 1 wherein the antibiotic-protein complex is concentrated by ultrafiltration, ion exchange or lyophilization.

8. A method according to claim 1 wherein the antibiotic-protein complex is lyophilized for long term storage.

9. A method according to claim 1 wherein the antibiotic is selected from the class consisting of anthracycline glycosides and derivatives and metabolites anthracyclinols, anthracyclinones and 7-deoxy-anthracyclinones.

10. A method according to claim 9 wherein said antibiotic is selected from the class consisting of adriamycin, N-trifluoroacetyl-14-valeryl-adriamycin, aclacinomycin A, daunomycin, 4-demethoxydaunomycin, 7-9-diepi-4-demethoxydaunomycin, 7-deoxydaunomycinone, (±)-aklavinone, iso-7-deoxydaunomycinone and 1,4-dihydroxy-5,8-bis-[[2-(hydroxyethyl)amino]ethyl]9,10-anthracenedione.

11. A water soluble light stable complex of antitumor antibiotics of the anthracycline and anthraquinone classes with purified apo riboflavin binding protein which comprises:
   (A) an antibiotic of the class consisting of (1) anthracyclines having the formula:

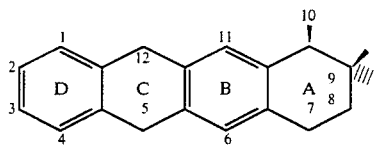

wherein positions 4, 5, 6, 7, 9, 10, 11 or 12 may be substituted, positions 5 and 12 have =O or OH, positions 4, 6 and 11 may have H, OH or $CH_3$, when positions 5 and 12 have =O, positions 6 and 11 have =O when positions 5 and 12 have OH, position 7 may have 7S or 7R chirality due to $OCH_3$ or any mono-, di-, or trisaccharide substituent, position 9 may have 9S or 9R chirality due to OH and either $CH_3$, $C_2H_5$, $COCH_2OH$ or $COCH_2OR$ where R is an ether or ester functional group, and position 10 may have 10S or 10R chirality due to $COCH_3$, $CO_2CH_2CH_3$ or $CO_2H$, and (2) anthraquinones having the formula:

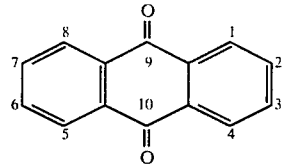

wherein positions 1, 4, 5 and 8 may be substituted, positions 1 and 4 may have H or OH, and positions 5 and 8 may have $N(CH_2)_2NH_2+(CH_2)_2OH$ or any bis[(hydroxyalkyl)amino]alkyl side chain, complexed with (B) purified apo riboflavin binding protein from eggs.

12. An antibiotic-protein complex according to claim 11 wherein said riboflavin binding protein is from chicken eggs.

13. An antibiotic-protein complex according to claim 11 wherein the complex is in aqueous solution in concentration between about 1 and 10 mM.

14. An antibiotic-protein complex according to claim 11 wherein the complex is a lyophilized powder.

15. An antibiotic-protein complex according to claim 11 wherein the antibiotic is selected from the class consisting of anthracycline glycosides and derivatives and metabolites anthracyclinols, anthracyclinones and 7-deoxy-anthracyclinones.

* * * * *